United States Patent [19]

Delbard

[11] Patent Number: Plant 5,673

[45] Date of Patent: Feb. 25, 1986

[54] HYBRID TEA ROSE PLANT CV. DELMATOR

[75] Inventor: Georges A. Delbard, Paris, France

[73] Assignee: Armstrong Nurseries, Inc., Ontario, Calif.

[21] Appl. No.: 612,005

[22] Filed: May 18, 1984

[51] Int. Cl.[4] ..... A01H 5/00

[52] U.S. Cl. ..... Plt./17

[58] Field of Search ..... Plt./17

*Primary Examiner*—Robert E. Bagwill

*Attorney, Agent, or Firm*—Synnestvedt & Lechner

[57] ABSTRACT

A new hybrid tea rose of the tall bush type, especially suited for greenhouse cut flower production. The new cultivar blooms nearly continuously throughout the year, producing an abundance of orange-red flowers, with petals reflexed outward at maturity, on long stems. Buds are characteristically long and pointed. The plant produces abundant, deep green foliage and displays above-average disease resistance.

1 Drawing Figure

This invention relates to a new variety of hybrid tea rose cv. Delmator. The plant is a greenhouse seedling of the tall bush type, cultivated for cut flower production. The plant's hardiness is as yet untested. It was first discovered by Georges A. Delbard in Evry, Essone, France, having as its seed parent an undisseminated seedling of (Zambra × Orange Sensation) and as its pollen parent an undisseminated seedling of [Zambra × (Orange Triumph × Floradora)]. Orange Sensation, Orange Triumph and Floradora are unpatented varieties; Zambra bears U.S. Plant Pat. No. 2,140.

The new rose cv. Delmator is particularly distinguishable from other commercialized rose cultivars by the following combination of characteristics: the relatively uniform orange-red coloration of its flowers, essentially as described and illustrated herein; its long, pointed bud form; its abundant and nearly continual year-round production of blooms borne on long cutting stems; its abundant deep green foliage; and its above-average disease resistance under Ontario, Calif., growing conditions. The variety holds these distinguishing characteristics through succeeding propagations by cutting and budding.

The new variety's seed parent, an unnamed and undisseminated seedling resulting from the cross (Zambra × Orange Sensation), is not available for direct comparison. However, the new rose may be distinguished from the named cultivars in the ancestry of its seed parent by the following combination of characteristics: Zambra bears flowers that are 2½ to 3 inches in diameter, with 10 to 15 petals per flower, whereas Delmator bears significantly larger flowers (4 to 4½ inches in diameter) of heavier petalage (23 to 27 petals), essentially as described and illustrated herein. Whereas Zambra produces flowers of a nasturtium orange color with a yellow reverse, the new rose produces flowers of a relatively uniform orange-red coloration. Orange Sensation bears flowers that are 3 to 3½ inches in diameter, whereas the new cultivar bears significantly larger flowers, 4 to 4½ inches in diameter. Whereas Orange Sensation is used primarily for garden decoration, Delmator is useful primarily as a greenhouse rose for cut flower production. Both Zambra and Orange Sensation are classified as floribunda roses, whereas the new rose is classified as a hybrid tea.

The new variety's pollen parent, an unnamed and undisseminated seedling resulting from the cross [Zambra × (Orange Triumph × Floradora)], is not available for direct comparison with Delmator. However, the new rose may be distinguished from the named cultivars in the ancestry of its pollen parent by the following combination of characteristics: The above comparison to Zambra as a seed parent ancestor would also apply to a comparison to Zambra as a pollen parent ancestor. Orange Triumph bears flowers of 1½- to 2-inch diameter, with 10 to 15 petals, whereas the new cultivar bears significantly larger flowers (4 to 4½ inches in diameter) of heavier petalage (23 to 27 petals per flower), essentially as described and illustrated herein. Orange Triumph is a polyantha rose used primarily for garden decoration, and Delmator is a hybrid tea used primarily in the greenhouse for cut flower production. Floradora bears flowers of 2 to 2½ inches in diameter, and the new cultivar bears significantly larger flowers of 4 to 4½ inches in diameter. Whereas Floradora is classified as a floribunda rose and is used primarily for garden decoration, Delmator is classified as a hybrid tea and is used primarily in the greenhouse for cut flower production.

The accompanying drawing illustrates the new variety in color as grown in Ontario, Calif., and shows the flowering thereof from bud to full bloom.

The descriptive matter which follows pertains to roses grown in Ontario, Calif., and is believed to apply to similar conditions of soil and climate elsewhere.

Throughout this specification, color names beginning with a small letter signify that the name of that color as used in common speech is aptly descriptive. Color names beginning with a capital letter designate values based upon The R.H.S. Colour Chart published by The Royal Horticultural Society of London, England.

FLOWER

The new variety usually bears its flowers singly, sometimes two or more to a stem, in irregular clusters on normal stems that are medium to long in length for the class. In the greenhouse, flowers are produced in very abundant quantities and nearly continuously throughout the growing season. Flower fragrance is slight and spicy.

BUD

The peduncle is average to long in length for the class, of slender to average caliper, and stiff. It is moderately smooth with some stipitate glands, and between Yellow-Green 144A and Green 137C in color.

Before the calyx breaks, the bud is medium to large for the class and of medium length, long, pointed and ovoid in form. There are many foliaceous appendages and stipitate glands on the surface of the bud, usually with slender, shallowly serrate foliaceous parts extending beyond the tip of the bud, equal to one half or more of its length.

As the calyx breaks, bud color is between Red 43A and Orange-Red 34B.

The inner surface of the sepals has a fine, woolly tomentum; margins are lined with stipitate glands and hairs.

As the first petal opens, the bud is average to large for the class, long and pointed to urn-shaped. Outside, the petals display a very small basal attachment zone of a color near Yellow 4A, which quickly suffuses to between Red 43A and Orange-Red 34C. Inside, the petals display a slightly larger basal attachment zone of a color near Green-Yellow 1A, which quickly suffuses to between Red 44B and Orange-Red 34B. The bud opens up well and is not prevented from opening by cold, hot or dry weather.

BLOOM

The size of the bloom when fully open is average to large for the class, from 4 to 4½ inches in diameter. The petalage is double with petals arranged regularly; petals number from 23 to 27, and there may be from 0 to 3 petaloids present. Bloom form when half-opened is very high centered, with petals moderately spiraled to cupped and with petal edges somewhat reflexed outward. When fully opened, the bloom is moderately cupped in form, with petals more loosely cupped and petal edges moderately reflexed outward.

Petals are of moderately heavy substance and are thick in texture, slightly velvety inside and slightly shiny to satiny outside. Outside petals are broadly obovate in shape with rounded apices. Intermediate petals are nearly round to broadly obovate, with rounded apices. Inside petals are narrowly obovate with rounded apices. Colors of all petals may be modified by being shaded or washed or tinted with other colors.

The following paragraph describes the color values observed in a newly opened flower from a plant of the new variety grown in a greenhouse in Ontario, Calif., in the month of December.

The outside surface of the outside, intermediate and inside petals has a small basal attachment zone near Yellow 4A, and the remainder of the petal surface quickly suffuses to between Red 40C and Orange-Red 34C. The inside surface of the outside, intermediate and inside petals displays a slightly larger basal attachment zone near Green-Yellow 1A, which quickly suffuses to between Red 40B and Orange-Red 34B.

The following paragraph describes the color values observed in a flower from a plant grown in a greenhouse in Ontario, Calif., that had been open for three days in the month of December.

The outside surface of the outside and inside petals has a small basal attachment zone of a color near Yellow 4B, and the remainder of the petal surface quickly suffuses to between Red 41C and Orange-Red 34D. The inside surface of the outside and inside petals has a slightly larger basal attachment zone, also of a color near Yellow 4B, which quickly suffuses in the remainder of the petals to between Red 41B and Orange-Red 34C.

The general color effect of a newly opened flower is between Red 40B and Orange-Red 34B, and the general color effect of a flower three days after opening is between Red 41B and Orange-Red 34C.

Petals usually drop off cleanly and are not particularly affected by cold, hot or dry weather. Flowers cut from plants grown in the greenhouse and kept at living-room temperatures last from five to seven days in the month of December.

REPRODUCTIVE ORGANS

Stamens are few to average in number and are arranged regularly about the pistils. Filaments are of medium length, and most have anthers. Anthers are small to medium in size; all open approximately at once. Color of the immature anthers is near Yellow-Orange 15B; color of the mature anthers is near Greyed-Orange 165A. Pollen is somewhat sparse and of a color near Yellow-Orange 16B.

Pistils are averge to many in number for the class (approximately 80). Styles are uneven, average to long in length, of thin caliper, and are somewhat loosely bunched. Stigma color is near Yellow 8C. Ovaries are usually all enclosed in the calyx.

Plants of the variety grown in Ontario, Calif., set short, globular hips of a color near Orange-Red 34B. The hips are moderately smooth with thick, fleshy walls.

Sepals are permanent and spear-shaped, medium to long in length, and have a color both inside and outside near Greyed-Orange 165A.

Seeds are of medium size and are produced in average quantity for the class (9 to 12 in number).

FOLIAGE

The compound leaves are moderately heavy and glossy, are borne in moderately abundant quantities, and usually comprise 3 to 5 leaflets of medium size for the class. Leaflets are oval in shape, having acute apices and round bases. Their margins are simply serrate.

The color of the upper surface of the young foliage is between Yellow-Green 147A and Green 136A, washed with near Greyed-Purple 183C; the under surface of the young foliage displays a coloration between Yellow-Green 147C and Green 138C, heavily washed with near Greyed-Purple 183B. When mature, the foliage displays an upper surface coloration of between Yellow-Green 147A and Green 136A and an under-surface coloration of between Yellow-Green 147C and Green 138C.

The rachis is average in size. Its upper side is grooved with some stipitate glands on the edges, while the underside is moderately smooth, with few stipitate glands.

Stipules are medium to long in length for the class, moderately narrow and have moderately long points turning out at an angle of usually more than 45°.

The plant displays a more-than-average resistance to mildew as compared with other cultivars now in commerce when grown under comparable conditions at Ontario, Calif.

GROWTH

Plants of the new variety are tall, upright, and much branched; canes are of medium caliper for the class. Plant growth is very vigorous.

The main stems are between Yellow-Green 146C and Green 139C in color and bear few to several large prickles which are of short to medium length for the class, almost straight with narrow bases that are of medium length, and near Greyed-Orange 177B in coloration. The main stems bear very few small prickles of a color near Greyed-Orange 177B. There are no hairs.

Branches are between Green 136B and Green 147B in color; they bear a few to several larger prickles which are of short to medium length for the class, almost straight, and have narrow bases of medium length. There are a few small prickles and a few hairs. Prickle and hair color is near Greyed-Orange 174D.

New shoots display the same coloration as the branches, washed lightly with near Greyed-Purple 183C. They bear few to several large prickles, which are of short to medium length for the class and are almost straight, having narrow bases of medium length.

The new shoots bear a few small prickles and a few hairs. Prickle and hair color is near Greyed-Orange 176C.

I claim:

1. A new and distinct variety of rose plant of the hybrid tea class, essentially as herein illustrated and described, being particularly characterized by its flowers of a uniform orange-red coloration; its long, pointed bud form; its abundant and nearly continual year-round production of blooms borne on long cutting stems; its abundant, deep green foliage; and its above-average disease resistance.

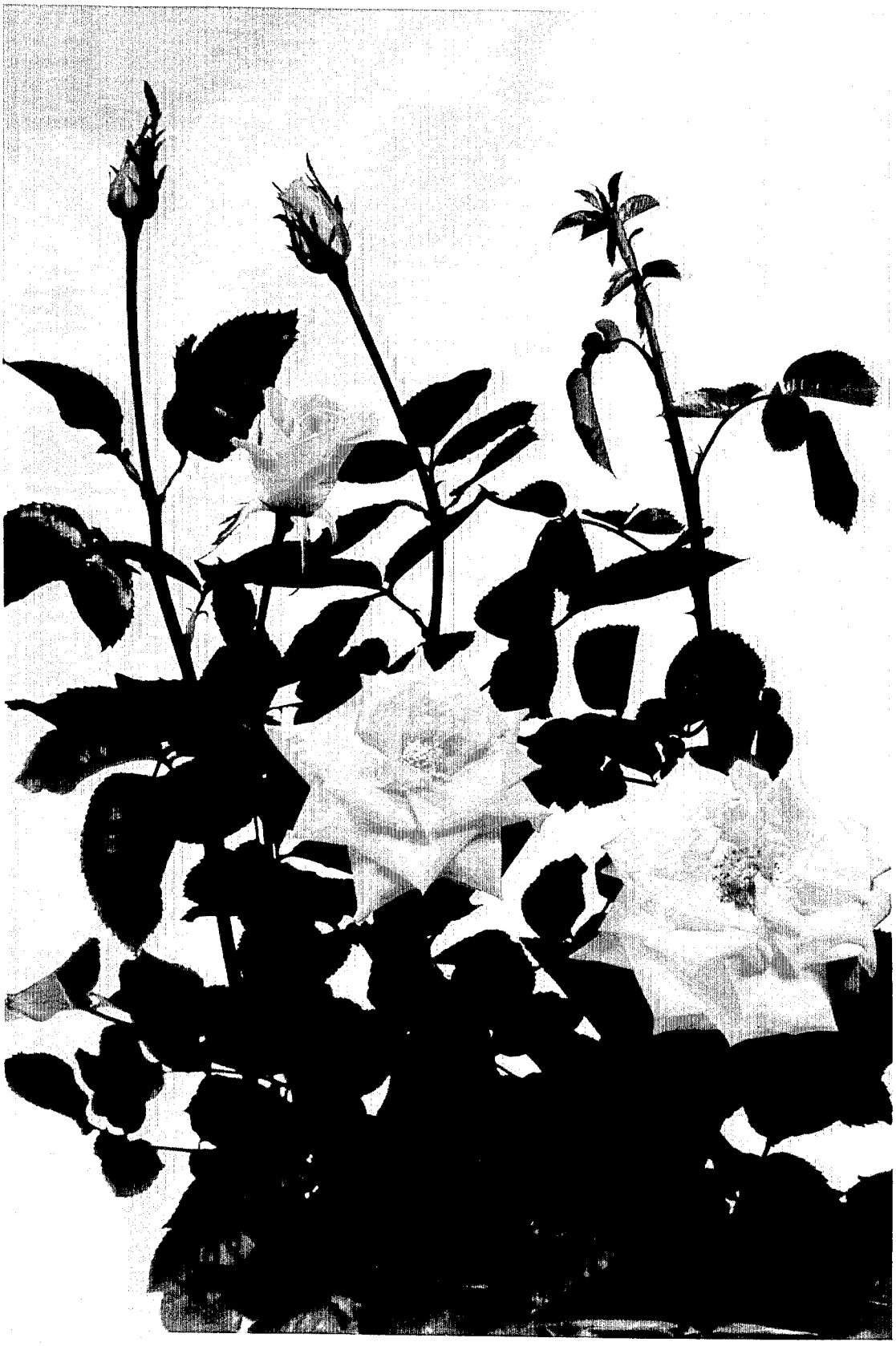

* * * * *